US012631576B2

(12) United States Patent
De Vries et al.

(10) Patent No.: US 12,631,576 B2
(45) Date of Patent: May 19, 2026

(54) IDENTIFYING CHARGE SHARING IN X-RAY DIFFRACTION

(71) Applicant: Malvern Panalytical B.V., Almelo (NL)

(72) Inventors: Roelof De Vries, Almelo (NL); Vladimir Jovanovic, Almelo (NL)

(73) Assignee: Malvern Panalytical B.V., Almelo (NL)

( * ) Notice: Subject to any disclaimer, the term of this patent is extended or adjusted under 35 U.S.C. 154(b) by 756 days.

(21) Appl. No.: 18/021,274

(22) PCT Filed: Aug. 24, 2021

(86) PCT No.: PCT/EP2021/073365
§ 371 (c)(1),
(2) Date: Feb. 14, 2023

(87) PCT Pub. No.: WO2022/043313
PCT Pub. Date: Mar. 3, 2022

(65) Prior Publication Data
US 2023/0293127 A1 Sep. 21, 2023

(30) Foreign Application Priority Data
Aug. 24, 2020 (EP) ..................................... 20192465

(51) Int. Cl.
*G01N 23/20008* (2018.01)
*A61B 6/42* (2024.01)
(52) U.S. Cl.
CPC ..... *G01N 23/20008* (2013.01); *A61B 6/4241* (2013.01)

(58) Field of Classification Search
CPC ........................ G01N 23/20008; A61B 6/4241
See application file for complete search history.

(56) References Cited

U.S. PATENT DOCUMENTS

2012/0112088 A1* 5/2012 Abraham ................ G01T 1/171
250/336.1
2019/0025440 A1* 1/2019 Steadman Booker .......................
G01T 1/2928
2022/0187477 A1* 6/2022 Steadman Booker .. G01T 1/171

FOREIGN PATENT DOCUMENTS

JP 2014-159973 A 9/2014
JP 2017-521682 A 8/2017

OTHER PUBLICATIONS

Dąbrowski, W., et al., "One Dimensional Detector for X-Ray Diffraction with Superior Energy Resolution Based on Silicon Strip Detector Technology," Jinst, Journal of Instrumentation, Institute of Physics Publishing, IOP Publishing for Sissa Medialab srl, vol. 7, No. 3, Mar. 8, 2012, pp. 1-21.

(Continued)

*Primary Examiner* — Carolyn Fin
(74) *Attorney, Agent, or Firm* — Cesari and McKenna, LLP

(57) ABSTRACT

An X-ray diffraction apparatus and method of processing signals from an X-ray diffraction apparatus are disclosed. By analysing a time delay between first and second pulses, generated by respective first and second detector cells, and by analysing an energy of each of the first pulse and the second pulse, charge sharing events and coincident photon events can be identified.

11 Claims, 5 Drawing Sheets

(56) References Cited

OTHER PUBLICATIONS

"European Search Report and Written Opinion," European Application No. 20192465.1-1001, Date of Mailing: Mar. 10, 2021, pp. 1-12.

Fredenberg, Erik, et al., "Energy Resolution of a Photon-Counting Silicon Strip Detector," Elsevier B. V., Elsevier, Nuclear Instruments and Methods in Physics Research A, vol. 613, No. 1, Jan. 21, 2010, pp. 156-162.

Lundqvist, Mats, "Silicon Strip Detectors for Scanned Multi-Slit X-Ray Imaging," Universitetsservice US AB, Vetenskap Och Konst, KTH, Kungl Tekniska Högskolan, Fysiska Institutionen, Stockholm, Sweden, Jan. 1, 2003, pp. 1-168.

"PCT International Search Report and the Written Opinion of the International Searching Authority" International Filing Date: Aug. 24, 2021, International Application No. PCT/EP2021/073365, Date of Mailing: Nov. 15, 2021, pp. 1-14.

"English Translation of Japanese Office Action," Japanese Patent Office, Japanese Patent Application No. 2023-513147, Date of Mailing: Apr. 15, 2025, pp. 1-2.

* cited by examiner

100

110 112 114 140

122

130 120

Readout Circuit 1 210a

140

Readout Circuit 2 210b

230

Detection Processor

114

Receive readout signals — 610

$(V_1 > V_D)$ AND $(V_2 > V_D)$? — 620

Yes

Detect first pulse and second pulse — 630

$\Delta t < T$? — 640

Yes

Determine that possible charge sharing has occurred — 650

$(V_L < V_1 < V_H)$ AND $(V_L < V_2 < V_H)$? — 660

No

Yes

Determine charge sharing — 680

670 — Determine coincident photons

Count neither pulse — 685

675 — Count both pulses

IDENTIFYING CHARGE SHARING IN X-RAY DIFFRACTION

CROSS-REFERENCE TO RELATED APPLICATIONS

The present application is the National Stage of International Application No. PCT/EP2021/073365, filed on Aug. 24, 2021, which claims priority from European patent application No. 20192465.1 filed on Aug. 24, 2020, the disclosure of both of which should be understood to be incorporated into this specification.

FIELD OF THE INVENTION

This invention relates to a method and apparatus for X-ray diffraction.

BACKGROUND OF THE INVENTION

X-ray diffraction (XRD) analysis is done by measuring the pattern of X-rays diffracted from a measurement sample, most often in one dimension over a range of diffraction angles. Solid-state 1D (strip) or 2D detectors can allow the measurement at several angles at the same time, thereby speeding up the overall measurement process. Moreover, the use of solid-state sensor materials and application-specific integrated-circuits (ASICs) for the sensor readout gives significantly lower noise levels and, in this way, can achieve better resolution of the energy of detected X-ray photons, when compared with older systems that were based on gas-filled detectors.

However, solid-state detectors, such as 1D strip detectors, can suffer from the problem of charge sharing, in which a single X-ray photon causes a response at two (typically adjacent) detector cells. When this happens, the energy of the photon may be divided between the two cells, giving the appearance of two photons of lower energies. This causes a reduction in the energy resolution of the XRD measurement.

It is known to try to address this problem by rejecting signals that arise substantially simultaneously in two adjacent detector cells. In other words, when two detector cells respond simultaneously, the system infers that charge sharing has occurred and both responses are discounted/disregarded—that is, a photon is not counted as having arrived at either of the two cells.

SUMMARY OF THE INVENTION

The known approach described above, of rejecting detector responses that occur simultaneously in adjacent detector cells, gives rise to a further drawback. It is possible that two real photons may arrive at the same time at neighbouring detector cells. The likelihood of this increases at higher X-ray intensities (for which the overall rate of incidence of photons is higher). Particularly at these higher intensities, the known rejection approach described above will have a deterioration in count rate linearity, because genuinely coincident photons are being mistakenly rejected as charge sharing events. According to an aspect of the present invention, there is provided an X-ray diffraction apparatus according to claim 1.

By examining the energy of each pulse, and counting only events where both pulses are of the correct energy (above $V_L$ and below $V_H$) the apparatus is able to count coincident photons of the desired type of X-ray radiation, while rejecting charge-shared photons and also photons at other energies, which are not desired to be counted for the X-ray diffraction measurement.

The inventors have recognised that examining the energy of the photons as well as their timing relationship can help to improve count rate linearity. By discriminating between charge sharing and genuine coincident photons, based on energy, the apparatus can reduce the number of genuinely coincident photons that are mistakenly discounted.

The inventors have also recognised that, by examining the energy of each of the two pulses separately, better discrimination of coincident photons from charge-shared photons (and other unwanted photons) may be possible. They have recognised that it is not sufficient to examine the aggregate energy detected in the two cells, for example, because this may still be susceptible to charge sharing caused by a photon at a higher energy than the X-ray photons of interest for the diffraction measurement. Embodiments of the present invention seek to address this. By examining the energy of each pulse individually, and setting an upper limit as well as a lower limit on the energy, the apparatus may be able to reject a photon of (undesired) K-beta X-ray radiation, even when charge sharing occurs and/or even when a photon of (desired) K-alpha X-ray radiation arrives simultaneously in an adjacent detector cell, for example.

Examining the individual pulse energies may improve robustness to noise, compared with analysing an aggregate of the energies, because noise in each signal may be combined additively when examining an aggregate measure (such as the sum of the two pulse energies). It also provides a relatively simple approach, avoiding unnecessary increase in the complexity of the circuits.

The detector may be a solid-state detector, comprising a semiconductor material.

The first and second detector cells may be positioned adjacent to one another—that is, at least having no other detector cells in between them. (In some implementations, electronic components other than detector cells may be positioned between the detector cells; however, it is desirable that the spaces between the detector cells be as small as possible.)

The detection processor may be provided as a separate component from the one or more readout circuits. The one or more readout circuits may be provided as one or more application specific integrated circuits (ASICs). The detection processor may be provided as a programmable processor, such as a digital signal processor (DSP), or as a reconfigurable processor, such as a field programmable gate array (FPGA).

Discounting the charge sharing event may mean that the detection processor does not count either of the pulses as an arrived photon, when it determines that a charge sharing event has occurred.

The first threshold may be selected to correspond to a photon energy that is less than a K-alpha emission line of the X-ray source. The second threshold may be selected to correspond to a photon energy that is greater than a K-alpha emission line of the X-ray source. Optionally, the second threshold may be selected to correspond to a photon energy that is less than a K-beta emission line of the X-ray source.

The detection processor and/or one or more readout circuits may be further configured to detect the existence of the first pulse and the second pulse on the basis of a detection threshold ($V_D$), wherein a pulse is detected only if its energy exceeds the detection threshold. The timing of each pulse (and therefore the time delay between pulses) may be determined by reference to the detection threshold. For example, to determine the time delay between two pulses, the detection processor may compare a time when the first pulse crossed the detection threshold with a time when the second pulse crossed the detection threshold. (The rising or falling edges of the respective pulses may be considered, in this context.)

The inventors have found that it is desirable to set the first and second thresholds so that they define a relatively narrow energy "window" about a characteristic X-ray energy of interest (such as a K-alpha emission line). This allows unwanted X-ray energies to be rejected. Meanwhile, to detect and reject charge sharing, it has been found advantageous to set the detection threshold at a relatively low level (close to the noise floor). Using a detection threshold that is different from each of the first and second thresholds enables both of these benefits to be achieved simultaneously.

The energy of a pulse may be determined by measuring its amplitude. Therefore, each of the first threshold, second threshold and detection threshold may be implemented as an amplitude threshold, in practice.

The one or more readout signals may be digital signals.

The one or more readout signals may indicate, for each detector cell, whether a pulse produced at that cell was: (i) above a detection threshold ($V_D$); (ii) above the first threshold ($V_L$); and (iii) above the second threshold ($V_H$), wherein the detection threshold is less than the first threshold, and the first threshold is less than the second threshold.

For example, a readout signal may comprise two bits per detector cell, encoding the values [0, 1, 2, 3]. The value 0 (binary '00') may represent the absence of any detected pulse. The value 1 (binary '01') may represent a pulse that exceeds the detection threshold, but does not reach the first threshold. The value 2 (binary '10') may represent a pulse that exceeds the first threshold but does not reach the second threshold; and the value 3 (binary '11') may represent a pulse that exceeds the second threshold. Of course, other encodings may also be used.

The one or more readout circuits may sample an output signal of each of the detector cells periodically to generate the one or more readout signals. For each detector cell, the time period between consecutive samplings of that detector cell may be less than 600 ns, preferably less than 400 ns, most preferably less than 200 ns. Frequent sampling is desirable in order to be able to accurately detect coincidence between photons.

The time period between consecutive samplings may be at least 10 ns, optionally at least 20 ns, 50 ns, or 100 ns or 150 ns. Sampling too frequently may have the drawback that large volumes of redundant data are collected.

The detector may comprise a third detector cell and a fourth detector cell, each being configured to convert incoming X-ray photons into respective electrical pulses, and wherein the one or more readout circuits comprise a first readout circuit and a second readout circuit, each coupled to the detector, wherein the first readout circuit is configured to receive electrical pulses from the first and third detector cells and generate a first readout signal for the detection processor, wherein the second readout circuit is configured to receive electrical pulses from the second and fourth detector cells and generate a second readout signal for the detection processor.

In this way the detection processor is able to discount charge sharing events occurring between cells that are read out by different readout circuits. This is an advantage of implementing the coincidence-detection processing separately from the readout circuit.

The detection processor may be configured to analyse, based on the first readout signal and the second readout signal, a third pulse generated by the third detector cell and a fourth pulse generated by the fourth detector cell, comprising:

if a time delay between the third pulse and the fourth pulse is less than a predetermined time threshold, determining that one of a charge sharing event and a coincident photon event has occurred, if an energy of each of the third pulse and the fourth pulse was above a first threshold ($V_L$) and below a second threshold ($V_H$), determining that a coincident photon event has occurred, and otherwise determining that a charge sharing event has occurred, the detection processor being further configured to count the coincident photon event as the arrival of an X-ray photon at each of the third and fourth detector cells, and to discount the charge sharing event.

The third detector cell may be positioned in the detector adjacent to the fourth detector cell. The second detector cell may be positioned in the detector between the first detector cell and the third detector cell.

The detector may be a 1D strip detector.

Also disclosed is a method of processing signals from an X-ray diffraction apparatus, according to claim 8.

Also provided is a computer program comprising computer program code configured to cause one or more physical computing devices to perform all the steps of a method according to an embodiment when said program is run on said one or more physical computing devices.

The computer program may be embodied on a computer readable medium. The computer readable medium may be a non-transitory computer readable medium.

BRIEF DESCRIPTION OF THE DRAWINGS

The invention will now be described by way of example with reference to the accompanying drawings, in which.

Figure 1:
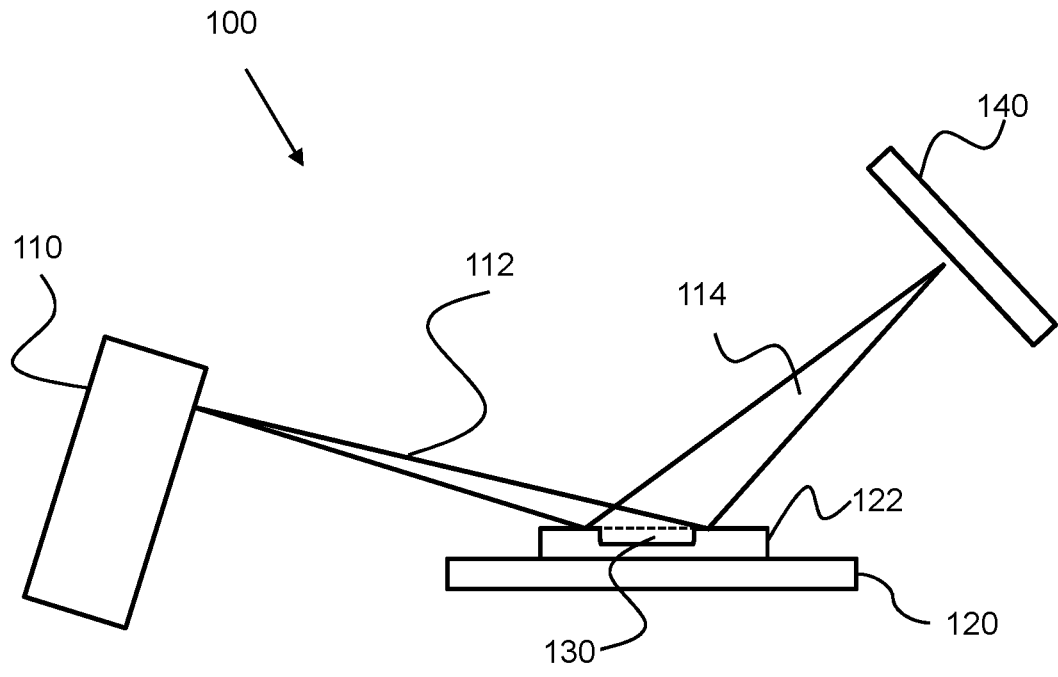
FIG. 1 is a schematic diagram of an X-ray diffraction apparatus according to an example.

It should be noted that these figures are diagrammatic and not drawn to scale. Relative dimensions and proportions of parts of these figures have been shown exaggerated or reduced in size, for the sake of clarity and convenience in the drawings.

DETAILED DESCRIPTION

It should be noted that the word "sample" is used in two specific, different contexts in this text. On the one hand, it is used as a noun to refer to the physical "sample" (or specimen) being investigated in an X-ray diffraction measurement. On the other hand, it is used as a verb to refer to the step of "sampling" an analog signal—for example as performed during an analog-to-digital conversion process. It is believed that the meaning of the word will be clear in each case, in light of the context of its usage.

FIG. 1 illustrates an X-ray diffraction apparatus 100 according to an example. The apparatus comprises an X-ray source 110, which in this example is an X-ray tube. It also comprises a sample stage 120, which supports a sample holder 122 holding a sample 130. The X-ray source 110 emits X-rays in an incident beam 112, which irradiates the sample 130. The sample 130 diffracts the X-rays, producing a diffracted beam 114. A detector 140 is provided, configured to receive and detect X-rays diffracted from the sample in the diffracted beam 114.

Figure 2:
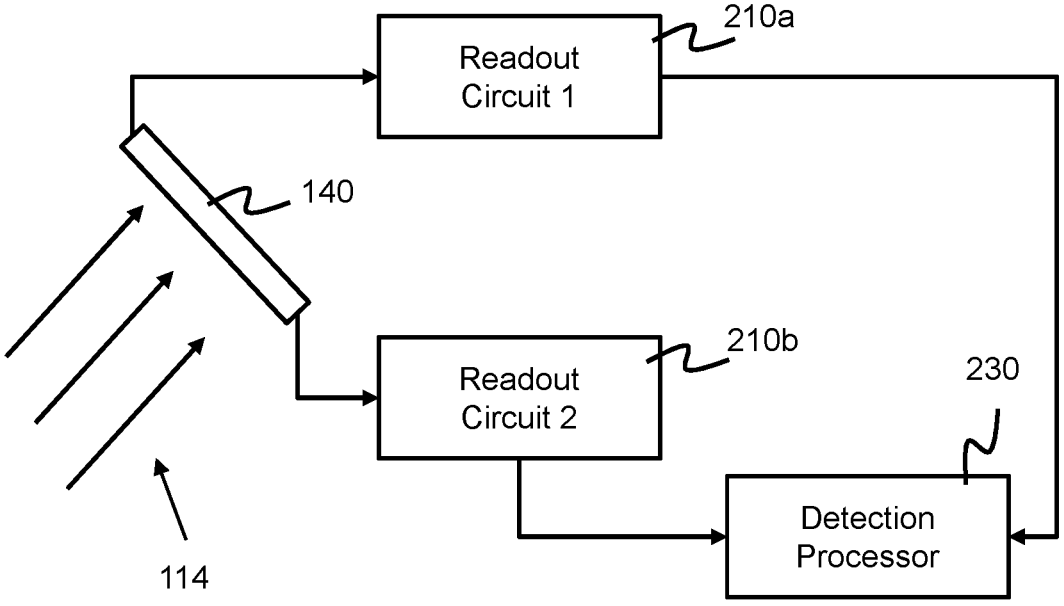
FIG. 2 is a block diagram showing the readout circuits and detection processor of the apparatus of FIG. 1.

FIG. 2 is a block diagram of an apparatus configured to process the output of the detector 140. First and second readout circuits 210*a*, 210*b* are coupled to the detector 140. The two readout circuits 210*a*, 210*b* communicate with a detection processor 230, which is configured to process the signals generated by the readout circuits. In the present example, the detection processor 230 is implemented by a programmable microprocessor. This allows the detection processing to be defined at least partially in software or firmware, which may increase flexibility by allowing the processing to be reconfigured for various different applications and measurements.

Figure 3:
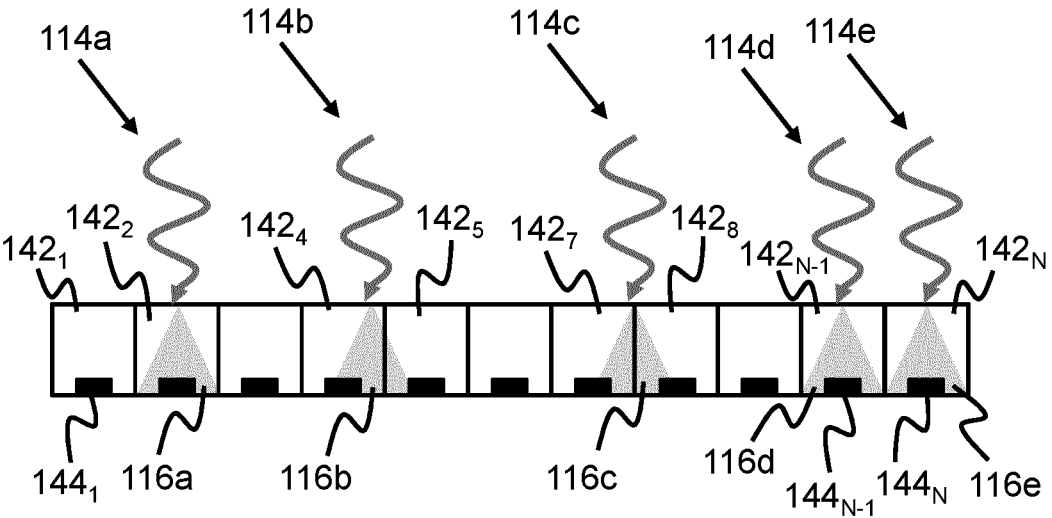
FIG. 3 is a schematic illustration of charge sharing and coincident photon events.

Before describing the operation of the apparatus in greater detail, the problem of charge sharing and coincident photons will firstly be explained, with reference to FIG. 3. FIG. 3 shows five X-ray photons 114*a-e* of the diffracted beam 114 incident on the detector 140. The detector comprises N detector cells $142_1$ to $142_N$. Each detector cell $142_1$ to $142_N$ comprises a respective detection element $144_1$ to $144_N$. In this example, the detector 140 is a microstrip detector, and each of the detection elements is a strip electrode. The arrival of each photon 114*a-e* generates a charge cloud (illustrated by shaded grey triangles 116*a-e*). The charge clouds are sensed by the detection elements 144, thereby converting the incoming X-ray photons into electrical pulses.

For the first photon 114*a*, there is in principle no problem, because all of the converted charge 116*a* is collected by a single strip of a single detector cell 1422. The generated charge will be transferred to a single preamplifier and the corresponding signal can be interpreted as the signal of one single photon, and is therefore representative of the energy of that photon (see below, with reference to FIG. 4).

The generated charge 116*b* of the second photon 114*b* is shared between the detector cells $142_4$ and $142_5$, and will be sensed by the respective strips (i.e. detection elements) of those cells. The charge collected by each strip represents a fraction of the energy of the incoming photon. This makes it impossible to deduce the energy of the photon, when considering a single channel, and will therefore cause deterioration of the energy resolution, biased to low energies. The same effect occurs for the generated charge 116*c* of the third photon 114*c*, which is shared between the detector cells $142_7$ and $142_8$.

The challenge posed can be explained by considering an example in which the X-ray source 110 is a tube using a copper (Cu) anode. This tube will give characteristic energies at 8 keV (K-alpha) and 8.9 keV (K-beta). If the strip detector has good intrinsic energy resolution (Full-Width Half-Maximum <400 eV @8 keV) it should be possible to only measure the 8 keV photons by only registering the events between 7.6 and 8.4 keV (for example). However, when an 8.9 keV photon is charge-shared between two channels, it might happen that one channel receives the charge equivalent to a signal of 8 keV and that an adjacent channel will receive the charge equivalent to a signal of 0.9 keV. If the apparatus is able to determine that both these events occur at the same time, it can infer that this photon must have had a different energy from the desired 8 keV energy and we can therefore discard it.

However, as mentioned previously above, examining only the timing of incidence to reject charge sharing has drawbacks, particularly when the intensity increases. The likelihood of two 8 keV photons arriving at two adjacent strips at the same time will increase. But, according to the logic mentioned above, these valid events will be discarded because they occur simultaneously. This means that the count rate linearity will drop severely at high count rates. The examples described below will attempt to mitigate this effect. FIG. 3 also shows two coincident photons 114*d* and 114*e* arriving substantially simultaneously at two adjacent detector cells $142_{N-1}$ and $142_N$. It would be desirable to detect and count these photons, rather than (wrongly) discount them as a charge-sharing event.

Figure 4:
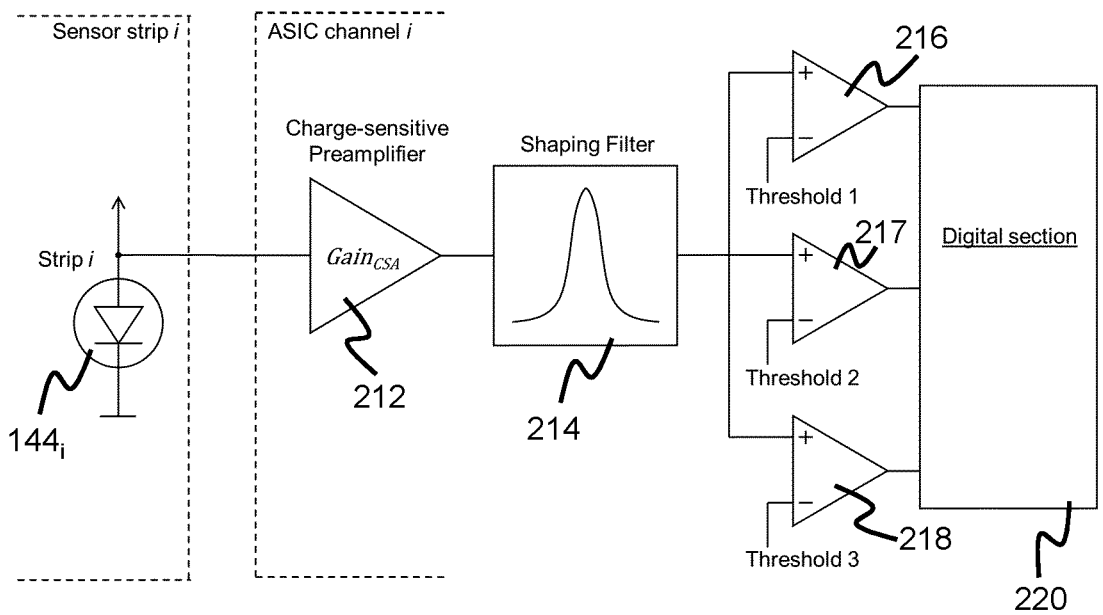
FIG. 4 is a block diagram illustrating the readout of a single detector cell in the detector of FIGS. 1 and 2.
Figure 5:
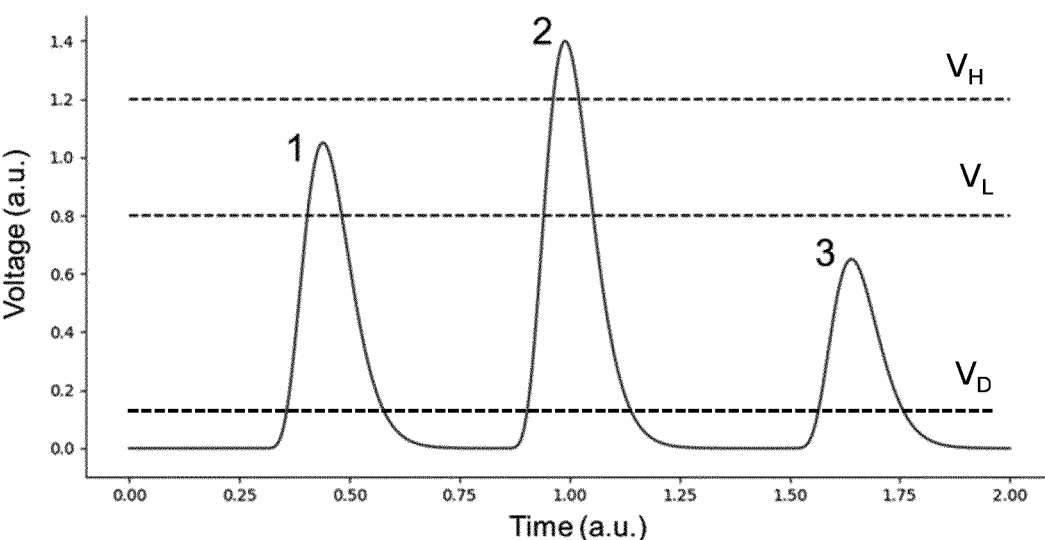
FIG. 5 illustrates how pulses generated by detector cells can be discriminated according to their amplitude.

FIG. 4 is a schematic diagram of a single channel of one of the readout circuits 210, according to an example. In the present example, the readout circuit 210 is implemented as an ASIC coupled to the detector 140. The detection element $144_i$ of the detector cell i in question is depicted as a diode. The corresponding channel i of the ASIC readout circuit 210 comprises a charge sensitive preamplifier 212 with a certain gain and a shaping filter 214. The preamplifier 212 and shaping filter 214 make up the analog front-end. The shaping filter 214 has a time constant, which influences the duration of the pulse output by the analog front-end. In some examples, there may be several selectable time constants (or several selectable shaping filters, each with a different time constant), which can be selected according to the required counting rate of the detected photons and the required energy resolution. Typically, shorter output pulses that are required for the higher counting rates contain more electronic noise which worsens energy resolution. After the analog front-end, the energy of the detected photon is evaluated by passing a voltage pulse generated by the photon through three comparators 216, 217, 218. The comparators detect whether the pulse height has crossed a threshold level, thereby digitizing the pulse amplitude (which is correlated with the photon energy). The first comparator 216 compares the pulse amplitude with a first threshold $V_L$; the second comparator 217 compares the pulse amplitude with a second threshold $V_H$; and the third comparator 218 compares the pulse amplitude with the third threshold, the detection threshold $V_D$. As illustrated in FIG. 5, the detection threshold $V_D$ is lower than the first threshold $V_L$; and the first threshold $V_L$ is lower than the second threshold $V_H$. Each of the thresholds may be configurable. Alternatively, some or all of them may be fixed—for example, hardwired into the ASIC design. The information digitized by the comparators is transferred from the readout circuit 210 to the detection processor 230, by digital section 220.

FIG. 5 illustrates the detection of different pulse amplitudes using the circuit of FIG. 4. Pulse 1 exceeds the first threshold $V_L$, but does not exceed the second threshold $V_H$. This is the energy range of interest (for example, the energy of a K-alpha line of the X-ray source). Pulse 2 exceeds the second threshold $V_H$. This would be the case for an unwanted K-beta line, for example. Pulse 3 exceeds the detection threshold $V_D$—and, accordingly, it is detected as a pulse—but it has a lower energy than the first threshold $V_L$.

In this example, pulse 1 would be counted but pulses 2 and 3 would be discounted (that is, ignored and not counted).

Note that, in the example described above, the exact connections between the individual detector cells 142 and the two readout circuits 210a and 210b were not described. This is because, in general, the apparatus is not limited to any particular arrangement of the connections. The two readout circuits can be used to increase the bandwidth for reading out data from the detector 140. This highlights an advantage of implementing detection processing in the detection processor 230 that is separate from the one or more readout circuits 210: the detection processor 230 has access to data from all of the detector cells, because it is connected to both of the readout circuits 210. In contrast, each individual readout circuit 210a, 210b only processes signals from a subset of the detector cells. Therefore, each readout circuit 210a, 210b can only detect charge sharing among the detector cells for which it is responsible.

Figure 6:
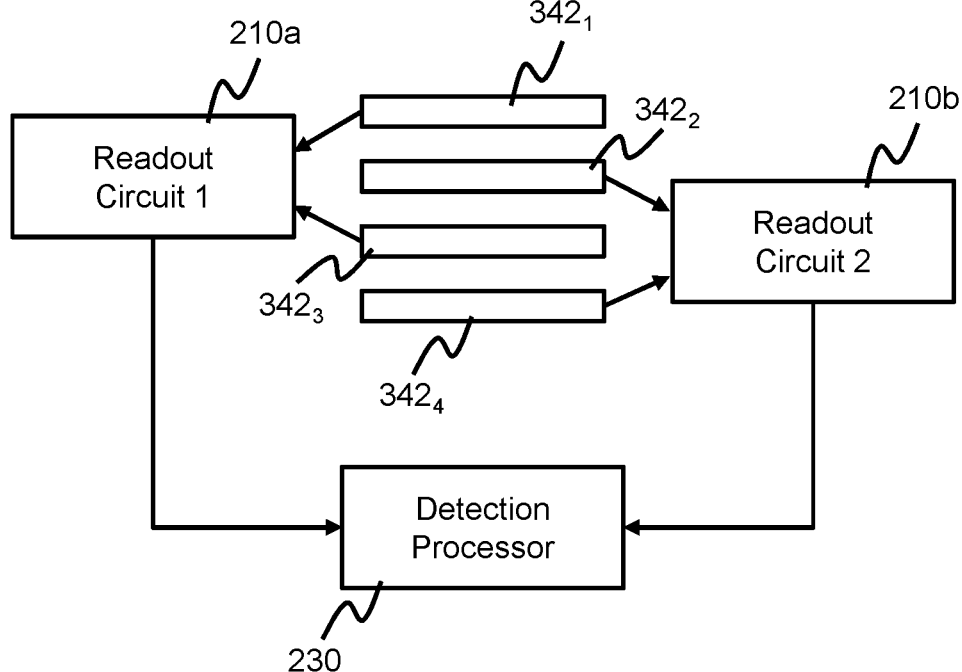
FIG. 6 is a block diagram showing readout circuits and a detection processor according to another example.

FIG. 6 shows an example in which the detection processor 230 is configured to detect charge sharing between adjacent detector cells whose signals are handled by different readout circuits 210. In this example, a first detector cell 342$_1$ and a third detector cell 342$_3$ are connected to a first readout circuit 210a. A second detector cell 342$_2$ and a fourth detector cell 342$_4$ are connected to a second readout circuit 210b. The second detector cell is positioned adjacent to and between the first and third detector cells. The third detector cell is positioned adjacent to and between the second and fourth detector cells.

Figure 7:
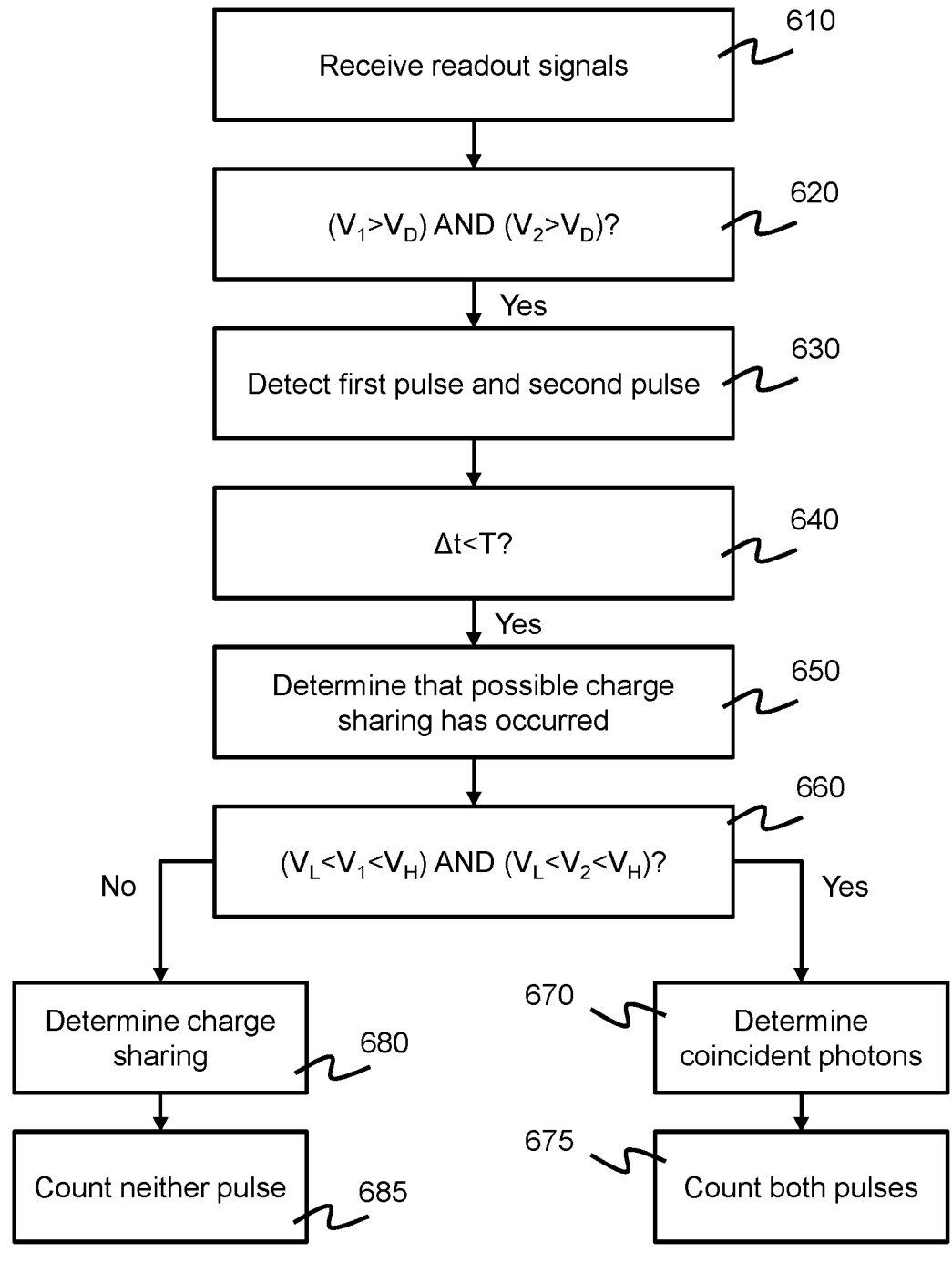
FIG. 7 is a flowchart illustrating a method according to an example.

A method performed by the XRD apparatus 100 will now be described, with reference to the flowchart of FIG. 7. The method of this example applies to the readout arrangement illustrated in FIG. 6, but also more generally to any readout arrangement, such as the one shown generically in FIG. 2.

In step 610, the detection processor 230 receives readout signals from the readout circuits 210. In this example, each readout circuit 210a, 210b is implemented as an ASIC; and the detection processor 230 is implemented as a programmable microprocessor. The readout signals are digital signals as described above with reference to FIG. 4. In particular, for each channel, each readout circuit 210 generates a 2-bit output. These two bits are capable of encoding four levels—indicating the following discrete cases for the pulse amplitude:

(i) there is no pulse—that is, the amplitude has not risen above the detection threshold;

(ii) there is a pulse, whose amplitude is above the detection threshold but below the first threshold;

(iii) there is a pulse, whose amplitude is above the first threshold but below the second threshold; or (iv) there is a pulse, whose amplitude is above the second threshold.

There are a total of 128 channels per readout circuit. Therefore, the number of detector cells is 256 (128×2). Each readout circuit 210 provides a 16-bit output at a clock rate of 100 MHz. The channels are multiplexed together in 16 groups of 8—that is, each 16-bit output consists of 8×2-bit digital values. For each readout circuit 210, the 16 groups of channels are output over 16 clock cycles. Two further clock cycles are used for synchronisation/handshaking with the detection processor 230, giving a total period of 18 cycles (180 ns) between successive samplings from the same detector cell appearing in the readout signal. A high sampling rate is desirable, to ensure accuracy in determining whether two pulses from adjacent cells were generated substantially simultaneously.

Let us assume that a first pulse with amplitude V$_1$ is generated by a first detection cell 142$_7$, and a second pulse with amplitude V$_2$ is generated by a second detection cell 142$_8$.

In step 620, the detection processor 230 evaluates whether the amplitudes V$_1$ and V$_2$ of each of the first pulse and the second pulse are greater than the detection threshold V$_D$. If both amplitudes are above the detection threshold, then the detection processor 210 detects the existence of the first and second pulses (step 630). Having established that there are two pulses to consider, the detection processor 230 next evaluates (in step 640) whether a time delay Δt between the two pulses is less than a predetermined time threshold T. If so, the detection processor treats the two pulses as having occurred substantially simultaneously. In the present example, pulses are treated as having occurred substantially simultaneously if they are detected in the readout signal within 640 ns of one another.

Note that, although charge sharing will generate pulses simultaneously in the two detector cells, small differences in the timing will be introduced by the digitisation in the readout circuit 210. As described above, the groups of channels are sampled and read out serially over a period of 180 ns. Furthermore, as the pulses are measured by comparing them with threshold amplitudes, the exact instant at which the pulse crosses a threshold is subject to jitter that depends on the amplitude of the pulse. Consequently, in practice, the detection processor 230 needs to consider a finite range of time differences, in order to detect substantially simultaneous pulses.

The optimal time threshold T is related to the pulse duration, which depends on the time constant of the shaping filter that is integrated behind the preamplifier. In the present example, the apparatus has four selectable time constants of the filter. The time threshold T should be approximately as long as a maximum possible time difference between two pulses generated by a charge-shared photon. In addition, a jitter due to digital readout should be added. This is why a fast digital readout is desirable. When the time constant of the shaping filter is changed, the time threshold T should be adapted accordingly (because the maximum possible time difference between charge-shared pulses is correlated with the time constant of the shaping filter). In the present example, good results were obtained with the time threshold T=640 ns and a time constant of 1.1 μs for the pulse shaping filter. This constant is the rise time for the pulse to reach its peak value (and the pulse requires approximately the same time to settle back down). In practice, the time threshold T is set less than this time constant because the detection threshold V$_D$ is not at the zero level. The time threshold T can easily be modified and can be adjusted depending on the level of the detection threshold, if necessary.

For completeness, note that, in the present example, the readout circuit 210 detects pulses on their falling (trailing) edge rather their rising (leading) edge. That is, the comparators 216-218 are triggered after the pulse rises above the respective threshold when the amplitude then falls back below it. The time delay between pulses is determined based on when the trailing edge of each pulse crosses back down below the detection threshold.

When it is determined, in step 640, that the time delay Δt is less than the threshold time T, the detection processor 230 determines (in step 650) that either a charge sharing event or a coincident photon event has occurred. In order to discriminate between these two possibilities, the detection processor 230 evaluates the pulse amplitudes relative to the first and second thresholds. In particular, in step 660, the detection processor 230 evaluates whether the amplitudes of both the first pulse and the second pulse are greater than the first threshold and less than the second threshold. If this is found to be the case, the detection processor 230 determines that a coincident photon event has occurred (step 670). That is, two photons have arrived at adjacent detector cells at substantially the same instant. On the other hand, if it is determined in step 660 that the amplitudes of the first and second pulses are not both between the first threshold and the second threshold, then the detection processor 230 determines that a charge sharing event has occurred (step 680). That is, the charge generated by at least one photon has been collected by two adjacent detector cells.

When the detection processor 230 determines that a coincident photon event has occurred, both pulses are counted as photons (step 675). When the detection processor 230 determines that a charge sharing event has occurred, neither pulse is counted as a photon (step 685).

The first and second thresholds may be chosen so that only coincident X-ray photons of a desired K-alpha characteristic transition energy are accepted as coincident photons. This can maximise the rejection of charge sharing events, and rejection of unwanted X-ray energies, while minimising the loss of count rate linearity at high intensities.

Note that if $\Delta t > T$, pulses are considered as being generated by separate events and are counted if they are inside the energy window (greater than $V_L$ and less than $V_H$). The coincidence check is done around each pulse for a time T before and a time T after the pulse. In the present example, the check considers the events only in adjacent cells.

A specific example of this method will now be described, referring to the apparatus of FIG. 6. As discussed above, in FIG. 6, the first readout circuit 210a reads out first and third pulses from first and third detector cells $342_1$ and $342_3$, and provides a first readout signal to the detection processor 230. The second readout circuit 210b reads out second and fourth pulses from second and fourth detector cells $342_2$ and $342_4$, and provides a second readout signal to the detection processor 230. The detection processor 230 analyses the pulses based on the first and second readout signals.

Figure 8:
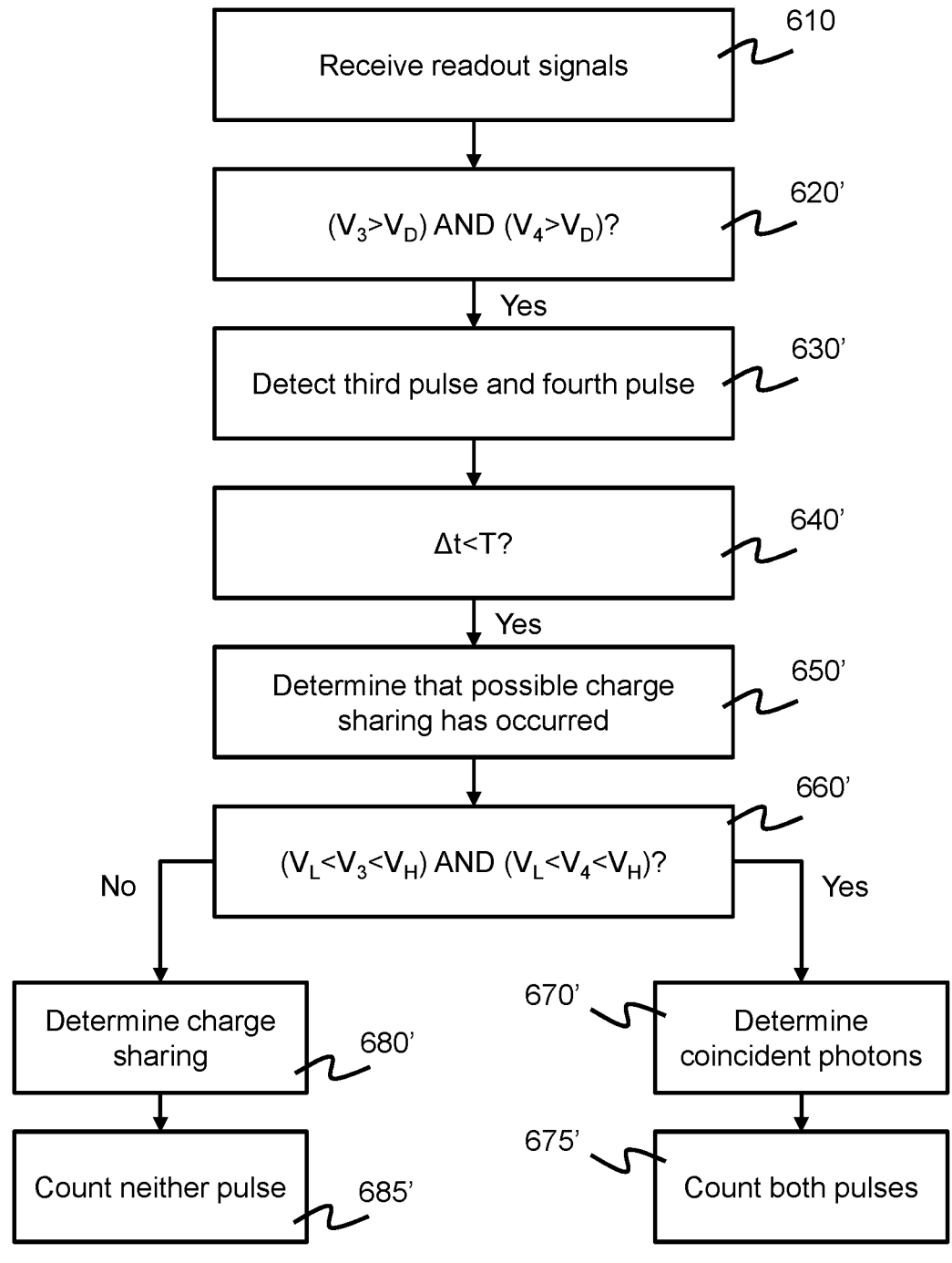
FIG. 8 is a flowchart illustrating a further method according to an example.

The first and second pulses are analysed as described above with reference to FIG. 7. The third and fourth pulses are analysed as illustrated in FIG. 8. The steps 620'-685' are substantially identical to their respective steps 620-685 in FIG. 7, except that the third and fourth pulses are evaluated instead of the first and second. Similar analysis may also be carried out to evaluate the second pulse, from the second detector cell, in comparison with the third pulse, from the third detector cell.

The foregoing example demonstrates some of the benefits of using a detection processor that is provided separately from the one or more readout circuits. This allows the detection processor 230 to be programmed or reconfigured easily. Moreover, it allows the detection processor 230 to evaluate potential charge sharing between all relevant pairings of detector cells, irrespective of whether the cells are read out by the first readout circuit 210a or the second readout circuit 210b.

Variations of the above-described examples are possible, without departing from the scope of the present disclosure. The following are some non-exhaustive examples of possible variations.

The time of the pulse may be established by its rising or falling edge. In the example described above, the readout circuit detected a pulse when the signal amplitude rose above at least the detection threshold and then fell back down below this threshold. In other words, each pulse was detected on its falling/trailing edge. Pulses could alternatively be detected on their rising/leading edge.

The description above has focused on the example of charge sharing between adjacent detector cells; however, the present invention is not necessarily limited to this. It is possible that charge sharing may occur between detector cells that are not immediately adjacent to one another, depending on the size and arrangement of the detector cells.

In the examples above, there were two readout circuits 210a and 210b. However, it will be understood that this is not essential. In other examples, there may be more than two readout circuits 210, or there may be just a single readout circuit 210.

In the examples described above, the detector was a 1D strip detector; however, the same principles can be applied to the detection and rejection of charge sharing for XRD measurements using a 2D solid-state detector.

It is not essential that the X-ray source be a copper source. Other sources will be known to those skilled in the art of XRD. Similar considerations and analysis apply to these other sources.

It should be noted that the above-mentioned examples illustrate rather than limit the invention, and that those skilled in the art will be able to design many alternative examples without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The examples may be implemented by means of hardware comprising several distinct elements. In a device claim enumerating several means, several of these means may be embodied by one and the same item of hardware. The mere fact that certain measures are recited in mutually different dependent claims does not indicate that a combination of these measures cannot be used to advantage. Furthermore in the appended claims lists comprising "at least one of: A; B; and C" should be interpreted as (A and/or B) and/or C.

Furthermore in general, the various examples may be implemented in hardware or special purpose circuits, software, logic or any combination thereof. For example, some aspects may be implemented in hardware, while other aspects may be implemented in firmware or software which may be executed by a controller, microprocessor or other computing device, although these are not limiting examples. While various aspects described herein may be illustrated and described as block diagrams, flow charts, or using some other pictorial representation, it is well understood that these blocks, apparatus, systems, techniques or methods described herein may be implemented in, as non-limiting examples, hardware, software, firmware, special purpose circuits or logic, general purpose hardware or controller or other computing devices, or some combination thereof.

The examples described herein may be implemented by computer software executable by a data processor of the apparatus, such as in the detection processor entity, or by hardware, or by a combination of software and hardware. Further in this regard it should be noted that any blocks of the logic flow as in the Figures may represent program steps, or interconnected logic circuits, blocks and functions, or a combination of program steps and logic circuits, blocks and functions. The software may be stored on such physical media as memory chips, or memory blocks implemented within the processor, magnetic media such as hard disk or floppy disks, and optical media such as for example CD-ROM or DVD.

The memory may be of any type suitable to the local technical environment and may be implemented using any suitable data storage technology, such as semiconductor-based memory devices, magnetic memory devices and systems, optical memory devices and systems, fixed memory and removable memory. The data processors may be of any type suitable to the local technical environment, and may include one or more of general purpose computers, special purpose computers, microprocessors, digital signal processors (DSPs), application specific integrated circuits (ASIC), gate level circuits and processors based on multi-core processor architecture, as non-limiting examples.

Examples as discussed herein may be practiced in various components such as integrated circuit modules. The design of integrated circuits is by and large a highly automated process. Complex and powerful software tools are available for converting a logic level design into a semiconductor circuit design ready to be etched and formed on a semiconductor substrate.

The invention claimed is:

1. An X-ray diffraction apparatus (100) comprising:

an X-ray source (110);

a sample stage (120), for receiving a sample to be irradiated by X-rays from the X-ray source;

a detector (140), arranged to receive X-rays diffracted from the sample;

one or more readout circuits (210), coupled to the detector; and a detection processor (230), configured to process signals generated by the one or more readout circuits to count a number of photons arriving at the detector, wherein the detector (140) comprises at least a first detector cell ($142_7$; $342_1$) and a second detector cell ($142_8$; $342_2$), each detector cell being configured to convert incoming X-ray photons into respective electrical pulses, wherein the one or more readout circuits (210) are configured to receive the electrical pulses from the first and second detector cells and generate one or more readout signals for the detection processor, wherein the detection processor (230) is configured to analyse, based on the one or more readout signals, a first pulse generated by the first detector cell and a second pulse generated by the second detector cell, comprising:

if a time delay between the first pulse and the second pulse is less than a predetermined time threshold, determining (650) that one of a charge sharing event and a coincident photon event has occurred, and if an energy of each of the first pulse and the second pulse was above a first threshold ($V_L$) and below a second threshold ($V_H$), determining (670) that a coincident photon event has occurred, and otherwise determining (680) that a charge sharing event has occurred, the detection processor being further configured to count (675) the coincident photon event as the arrival of an X-ray photon at each of the first and second detector cells, and to discount (685) the charge sharing event.

2. The apparatus of claim 1, wherein the one or more readout signals are digital signals.

3. The apparatus of claim 1, wherein the one or more readout signals indicate, for each detector cell, whether a pulse produced at that cell was:

(i) above a detection threshold ($V_D$);

(ii) above the first threshold ($V_L$); and (iii) above the second threshold ($V_H$), wherein the detection threshold is less than the first threshold, and the first threshold is less than the second threshold.

4. The apparatus of claim 1, wherein the one or more readout circuits (210) sample an output signal of each of the detector cells (142) periodically to generate the one or more readout signals.

5. The apparatus of claim 1, wherein the detector (140) comprises a third detector cell ($342_3$) and a fourth detector cell ($342_4$), each being configured to convert incoming X-ray photons into respective electrical pulses, and wherein the one or more readout circuits comprise a first readout circuit (210a) and a second readout circuit (210b), each coupled to the detector (140), wherein the first readout circuit (210a) is configured to receive electrical pulses from the first and third detector cells ($342_1$, $342_3$) and generate a first readout signal for the detection processor (230), wherein the second readout circuit is configured to receive electrical pulses from the second and fourth detector cells ($342_2$, $342_4$) and generate a second readout signal for the detection processor (230).

6. The apparatus of claim 5, wherein the third detector cell ($342_3$) is positioned in the detector adjacent to the fourth detector cell ($342_4$).

7. The apparatus of claim 1, wherein the detector (140) is a 1D strip detector.

8. A method of processing signals from an X-ray diffraction apparatus (100), the apparatus comprising a detector (140) arranged to receive X-rays diffracted from the sample, the detector comprising at least a first detector cell ($142_7$; $342_1$) and a second detector cell ($142_8$; $342_2$), each detector cell being configured to convert incoming X-ray photons into respective electrical pulses, the method comprising:

obtaining (610) one or more readout signals describing a first pulse generated by the first detector cell and a second pulse generated by the second detector cell; and analysing, based on the one or more readout signals, the first pulse and the second pulse, comprising:

if a time delay between the first pulse and the second pulse is less than a predetermined time threshold, determining (650) that one of a charge sharing event and a coincident photon event has occurred, and if an energy of each of the first pulse and the second pulse was above a first threshold ($V_L$) and below a second threshold ($V_H$), determining (670) that a coincident photon event has occurred, and otherwise determining (680) that a charge sharing event has occurred, the method further comprising counting (675) the coincident photon event as the arrival of an X-ray photon at each of the first and second detector cells, and discounting (685) the charge sharing event.

9. The method of claim 8, wherein the one or more readout signals are digital signals.

10. The method of claim 8, wherein the one or more readout signals indicate, for each detector cell, whether a pulse produced at that cell was:

(i) above a detection threshold ($V_D$);

(ii) above the first threshold ($V_L$); and (iii) above the second threshold ($V_H$), wherein the detection threshold is less than the first threshold, and the first threshold is less than the second threshold.

11. A non-transitory computer readable storage medium storing a program comprising computer program code configured to cause one or more physical computing devices to perform all the steps of claim 8 when process signals from an X-ray diffraction apparatus (100), the apparatus comprising a detector (140) arranged to receive X-rays diffracted from the sample, the detector comprising at least a first detector cell (142$_7$; 342$_1$) and a second detector cell (142$_8$; 342$_2$), each detector cell being configured to convert incoming X-ray photons into respective electrical pulses, said program, when executed is run on said one or more physical computing devices operable to:

obtain (610) one or more readout signals describing a first pulse generated by the first detector cell and a second pulse generated by the second detector cell;

analyse, based on the one or more readout signals, the first pulse and the second pulse, comprising:

if a time delay between the first pulse and the second pulse is less than a predetermined time threshold, determine (650) that one of a charge sharing event and a coincident photon event has occurred, and if an energy of each of the first pulse and the second pulse was above a first threshold ($V_L$) and below a second threshold ($V_H$), determine (670) that a coincident photon event has occurred, and otherwise determining (680) that a charge sharing event has occurred; and count (675) the coincident photon event as the arrival of an X-ray photon at each of the first and second detector cells, and discounting (685) the charge sharing event.

* * * * *